(12) United States Patent
Leavitt

(10) Patent No.: US 6,370,264 B1
(45) Date of Patent: Apr. 9, 2002

(54) METHOD AND APPARATUS FOR ULTRASONIC COLOR FLOW IMAGING

(76) Inventor: Steven C Leavitt, 800 Bulfinch Dr. Apt. 505, Andover, MA (US) 01810

( * ) Notice: Subject to any disclaimer, the term of this patent is extended or adjusted under 35 U.S.C. 154(b) by 0 days.

(21) Appl. No.: 09/287,980

(22) Filed: Apr. 7, 1999

(51) Int. Cl.[7] .................................................. G06K 9/00
(52) U.S. Cl. ....................................................... 382/128
(58) Field of Search ................................. 382/128, 130, 382/131; 348/163; 600/437, 443, 449, 454, 455, 465, 468; 128/915, 916; 73/1.82, 703, 861.18, 861.25

(56) References Cited

U.S. PATENT DOCUMENTS

| | | | |
|---|---|---|---|
| 4,468,747 A | | 8/1984 | Leavitt et al. ............... 348/163 |
| 4,471,449 A | | 9/1984 | Leavitt et al. ............... 600/455 |
| 4,850,364 A | | 7/1989 | Leavitt ........................ 600/455 |
| 4,932,415 A | * | 6/1990 | Angelsen et al. ........... 600/455 |
| 5,107,466 A | * | 4/1992 | Nishiyama et al. .......... 367/90 |
| 5,429,137 A | | 7/1995 | Phelps et al. ................ 600/455 |
| 6,148,224 A | * | 11/2000 | Jensen ......................... 600/407 |
| 6,176,828 B1 | * | 1/2001 | Becker et al. ............... 600/440 |
| 6,186,950 B1 | * | 2/2001 | Averkiou et al. ............ 600/443 |

* cited by examiner

Primary Examiner—Andrew W. Johns
Assistant Examiner—Shervin Nakhjavan

(57) ABSTRACT

A flow velocity processor for use in a color flow imaging system having reduced dynamic range requirements with an improved segmentation scan conversion on a pixel by pixel decision using velocity data derived from an autocorrelation vector after conversion to a unit vector, a compressed magnitude of the autocorrelation vector, and the two dimensional magnitude information. An autocorrelation vector processor generates autocorrelation vectors between pairs of N complex samples of at least one set of complex samples, each autocorrelation vector having amplitude and phase information. A unit vector convertor generates a corresponding unity amplitude autocorrelation vector for each processed input set of N complex samples, the phase of each unit amplitude autocorrelation vector being the same as the resultant autocorrelation vector, and the two components of the unit amplitude autocorrelation vector are used for subsequent calculation of the velocity and segmentation into a final color flow image. An autocorrelation vector magnitude information processing path may extract the amplitude component of each autocorrelation vector, generating compressed autocorrelation vector amplitude information for generation of a segmented image and a two dimensional image data processing path may extract two dimensional image data for the generation of a final segmented image. A scan convertor translates polar space data resampled rectangular space data and the two components of the unit vector are converted to a velocity value and, along with the compressed amplitude data and the two dimensional data, are ready for segmentation to generate the final display image.

10 Claims, 4 Drawing Sheets

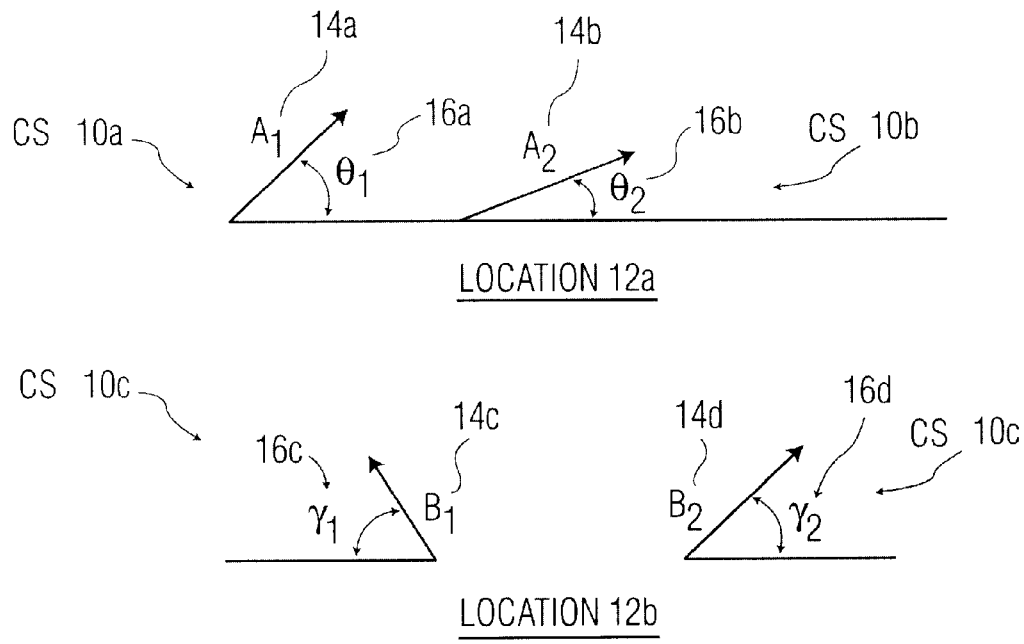

FIG. 1A
PRIOR ART $$CS\ 10a = A_1 @^{j\theta_1} \quad \longleftarrow 18a$$

$$CS\ 10b = A_2 @^{j\theta_2} \quad \longleftarrow 18b$$

$$V_A\ 20a = A_1 A_2 @^{j(\theta_2 - \theta_1)} \quad \longleftarrow 18c\text{-}1$$

$$= A_1 A_2 (\cos(\theta_2 - \theta_1) + j \sin(\theta_2 - \theta_1)) \quad \longleftarrow 18c\text{-}2$$

$$= A_1 A_2 \cos(\theta_2 - \theta_1) + j A_1 A_2 \sin(\theta_2 - \theta_1) \quad \longleftarrow 18c\text{-}3$$

$$\text{Real } V_A\ 20r = A_1 A_2 \cos(\theta_2 - \theta_1) = A_{21} \cos \theta_{21} \quad \longleftarrow 18d\text{-}1$$

$$\text{Real } V_A\ 20i = A_1 A_2 \sin(\theta_2 - \theta_1) = A_{21} \sin \theta_{21} \quad \longleftarrow 18d\text{-}2$$

FIG. 1B
PRIOR ART $$CS\ 10c = B_1\ @^{j\gamma_1} \quad\longleftarrow 22a$$
$$CS\ 10d = B_2\ @^{j\gamma_2} \quad\longleftarrow 22b$$

$$V_B\ 20b = B_1 B_2\ @^{j(\gamma_2-\gamma_1)} \quad\longleftarrow 22c\text{-}1$$
$$= B_1 B_2\ (\cos(\gamma_2-\gamma_1)) + j\sin(\gamma_2-\gamma_1) \quad\longleftarrow 22c\text{-}2$$
$$= B_1 B_2 \cos(\gamma_2-\gamma_1) + j\, B_1 B_2 \sin(\gamma_2-\gamma_1) \quad\longleftarrow 22c\text{-}3$$

$$\text{Real } V_B\ 20r = B_1 B_2 \cos(\gamma_2-\gamma_1) = B_{21}\cos\gamma_{21} \quad\longleftarrow 22d\text{-}1$$
$$\text{Imag } V_B\ 20i = B_1 B_2 \sin(\gamma_2-\gamma_1) = B_{21}\sin\gamma_{21} \quad\longleftarrow 22d\text{-}2$$

$$\text{Real Int } 24r = K(A_{21}\cos\theta_{21}) + (1-K)(B_{21}\cos\gamma_{21}) \quad\longleftarrow 24\text{-}1$$
$$\text{Imag Int } 24i = K(A_{21}\sin\theta_{21}) + (1-K)(B_{21}\cos\gamma_{21}) \quad\longleftarrow 24\text{-}2$$

FIG. 1C
PRIOR ART $$V_A\ 20a = A_1 A_2 \cos(\theta_2-\theta_1) + j\, A_1 A_2 \sin(\theta_2-\theta_1) \quad\longleftarrow 26a\text{-}1$$
$$V_B\ 20b = B_1 B_2 \cos(\gamma_2-\gamma_1) + j\, B_1 B_2 \sin(\gamma_2-\gamma_1) \quad\longleftarrow 26a\text{-}2$$

FIG. 2A $$V_A\ 20a' = \cos(\theta_2-\theta_1) + j\sin(\theta_2-\theta_1) \quad\longleftarrow 28a\text{-}1$$
$$V_B\ 20b' = \cos(\gamma_2-\gamma_1) + j\sin(\gamma_2-\gamma_1) \quad\longleftarrow 28a\text{-}2$$

$$\text{Real } V_A\ 20r' = \cos\theta_{21} \quad\longleftarrow 28b\text{-}1$$
$$\text{Imagl } V_A\ 20i' = \sin\theta_{21} \quad\longleftarrow 28b\text{-}2$$
$$\text{Real } V_B\ 20r' = \cos\gamma_{21} \quad\longleftarrow 28c\text{-}1$$
$$\text{Imagl } V_B\ 20i' = \sin\gamma_{21} \quad\longleftarrow 28c\text{-}2$$

$$\text{Real Int } 24r' = K\cos\theta_{21} + (1-K)\cos\gamma_{21} \quad\longleftarrow 28\text{-}1$$
$$\text{Imag Int } 24i' = K\sin\theta_{21} + (1-K)\sin\gamma_{21} \quad\longleftarrow 28\text{-}2$$

FIG. 2B

METHOD AND APPARATUS FOR ULTRASONIC COLOR FLOW IMAGING

TECHNICAL FIELD

The present invention relates to improved methods and apparatus for ultrasonic imaging of color flow data representing, for example, the flow of blood in the chambers of a heart and, in particular, to an improved method and apparatus for ultrasonic color flow imaging wherein flow velocity data is generated by separately processing the velocity vector phase information and the velocity vector magnitude information and wherein three forms of image data, the velocity data derived from phase components of the autocorrelation vectors, the compressed amplitude of autocorrelation vectors, and two dimensional (2D) image amplitude information, are provided for generating segmented images on a pixel by pixel basis wherein segmentation is the process of displaying velocity information or anatomical 2D information at a specific location.

BACKGROUND ART

Ultrasonic transducers and imaging systems are used in many medical applications and, in particular, for the non-invasive acquisition of images of cross sections of organs and conditions within a patient, typical examples being the ultrasound imaging of fetuses and the heart. Such systems commonly use a phased array transducer having multiple transmitting and receiving elements to transmit and receive narrowly focused and "steerable" beams, or "lines", of ultrasonic energy into and from the body. The transmitted beams, or lines, are reflected from the body's internal structures and received as beams, or lines, that contain information that is used to generate images of the body's internal structures.

In a typical application, such as cardiac scanning, a number of beams or lines are transmitted and received along a plurality of angles forming a sector, that is, a wedge of finite thickness, wherein the angular width of a sector may be the full range of angles that the transducer is capable of generating and receiving, or a selected portion of that range. A volume is interrogated, rather than a plane, due to the transmit and receive beam having a finite elevation thickness. The lines of a sector are typically then organized into "frames" wherein each frame contains data representing a volume of interest, that is, a sector, and may be further processed or viewed to extract or present the information of interest, such as an image of the volume of interest over a part or the whole of a cardiac cycle.

One important application of ultrasonic imaging is color flow mapping wherein doppler information is extracted from the returning signals, that is, scan lines, to generate images, or maps, of blood flow velocity in, for example, the chambers of a heart. Color flow mapping, however, requires more data acquisitions than does anatomic 2D imaging of a volume of interest of a heart and more extensive and complex processing of the input data, that is, the scan lines.

As a consequence, the color flow mapping systems of the prior art have generally required complex and expensive hardware to perform the color flow data processing operations, thereby increasing the cost of color flow mapping and limiting the use of color flow mapping.

In addition, the methods of the prior art for processing color flow data to generate color flow images have frequently resulted in inherent errors in or degradation of the color flow mapping images because of unwanted effects from the processing methods themselves. For example, a typical method for color flow mapping involves determining the autocorrelation vectors from the real and imaginary components of the complex samples taken at an array of locations in the region of interest and the subsequent complex scan conversion of the real and imaginary components of the autocorrelation vectors to generate the components of the color flow map. Each resultant autocorrelation sum, or velocity vector, represents the direction and magnitude of motion of an "object" wherein these "objects" may be a collection of red blood cells or moving tissue. As a consequence of the autocorrelation, the velocity vectors are typically scan converted from the input polar coordinate space to an x-y cartesian space. Since the real and imaginary components must be converted to velocity using trigonometric relationships, the full dynamic range of the components must be preserved through scan conversion, thereby creating a significant design issue in preserving the dynamic range of the components within an acceptable number of data bits.

In the prior art, segmentation may be done prior to scan conversion in order to alleviate the need to carry the magnitude of the autocorrelation vector through scan conversion, thereby enabling scan conversion of unit autocorrelation vectors only. The segmentation done prior to scan conversion would use the amplitude and phase of the autocorrelation vectors along with the two dimensional amplitude to decide on a sample by sample basis whether to keep the autocorrelation value, and ultimately the flow velocity, or keep the two dimensional sample. After segmentation, the autocorrelation vectors may be converted to unit amplitude vectors for subsequent scan conversion, thereby eliminating the dynamic range problem. The problem with segmentation at the sample level is that each decision affects many pixels after scan conversion, resulting in large flow voids scattered throughout the image. Solving the dynamic range scan conversion in this way causes unnecessarily large flow voids.

The present invention provides a solution to these and other problems of the prior art.

SUMMARY OF THE INVENTION

The present invention is directed to a flow velocity processor for use in a color flow imaging system having reduced dynamic range requirements for subsequent scan conversion of velocity image information, and the method for processing flow velocity information to provide reduced dynamic range requirements. In addition, an improved segmentation method based on a pixel by pixel decision after scan conversion using three components, the velocity data derived from the autocorrelation vector after conversion to a unit vector, a compressed magnitude of the autocorrelation vector, and the two dimensional magnitude information.

The ultrasonic flow imaging system typically includes an ultrasonic scan array of transducer elements for transmitting and receiving scan lines, a beamformer for forming transmitting and receiving scan lines, and a scan line signal processor for detecting received scan lines and generating two dimensional acoustic samples and complex samples representing image flow information wherein each complex sample conveys both amplitude and phase information.

According to one embodiment of the present invention, the flow velocity processor includes an autocorrelation vector processor for generating autocorrelation vectors between pairs of complex samples of at least one input set of N complex samples wherein N is at least two and wherein each autocorrelation vector includes both amplitude and phase information. The flow velocity processor further includes a unit vector convertor for generating a corresponding unity amplitude autocorrelation vector for each processed input set of N complex samples. The phase of each unit amplitude autocorrelation vector is the same as the resultant autocorrelation vector. The two components of the unit amplitude autocorrelation vector are inputted to a scan convertor for subsequent calculation of the velocity and segmentation into a final color flow image.

The flow velocity processor may also include an autocorrelation vector magnitude information processing path for extracting the amplitude component of each autocorrelation vector, generating compressed autocorrelation vector amplitude information, and providing the compressed vector amplitude information to the scan convertor for generation of a final segmented image.

The color flow imaging system may further include a two dimensional image data processing path for extracting two dimensional image data from the received scan lines and providing the two dimensional image data to the scan convertor for the generation of a final segmented image.

In other aspects, the color flow imaging system includes a scan convertor capable of translating data collected in polar space to data resampled in rectangular space. The four outputs from the scan convertor, the two components of the unit vector, the compressed amplitude data and the two dimensional data, are further processed by the flow velocity processor. The two components of the unit vector are converted to a velocity value and, along with the compressed amplitude data and the two dimensional data, are ready for segmentation to generate the final display image.

Other features of the present invention will be understood by those of ordinary skill in the art after reading the following descriptions of a present implementation of the present invention, and after examining the drawings, wherein:

BRIEF DESCRIPTION OF THE DRAWINGS

FIGS. 1A, 1B and 1C illustrate the methods of the prior art for generation of autocorrelation vectors representing velocity from complex samples;

FIGS. 2A and 2B illustrate the method of the present invention for generation of autocorrelation vectors of the present invention;

BEST MODE FOR CARRYING OUT THE INVENTION

Figure 3A:
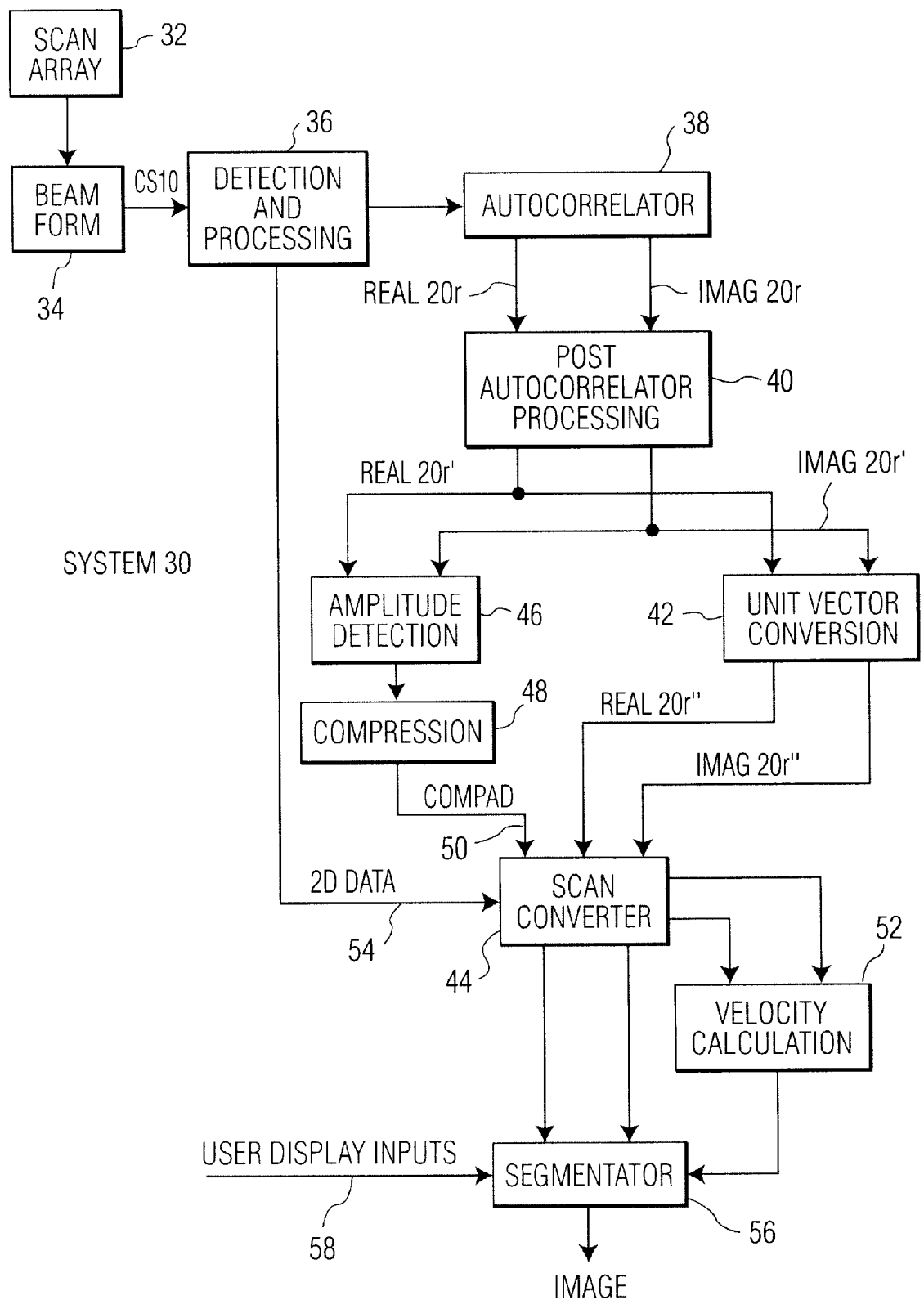
FIG. 3A is a block diagram of an exemplary system incorporating the present invention.

The following will first describe a typical method of the prior art for processing color flow data and will then describe the method of the present invention for processing color flow data, after which an improved system implementing the present invention will be described.

A. A Method of the Prior Art for Color Flow Mapping (FIGS. 1A, 1B and 1C)

As described above, a typical method of the prior art for color flow mapping involves first determining the autocorrelation vectors of the real and imaginary components of velocity vectors represented by complex samples, that is, samples of received signals having real and imaginary components, taken at an array of locations in the region of interest, and subsequently performing a complex scan conversion of the real and imaginary components of the autocorrelation vectors to generate the components of the color flow image. As described, each complex sample is comprised of a vector magnitude component representing the amplitude of the received signal and a vector angle or phase component of the received signal. The real and imaginary components are typically scan converted as a complex pair preserving the phase and amplitude information contained in the original vector. This requires one to use a sufficient number of bits in the digital scan converter to preserve the dynamic range of the signal.

This may be shown by reference to FIG. 1A, which together with FIGS. 1B and 1C illustrate the operation of a color flow imaging system of the prior art that utilizes complex scan conversion of the real and imaginary components of velocity autocorrelation vectors to generate a color flow image, such as that described in U.S. Pat. No. 5,429,137, issued Jul. 4, 1995.

As illustrated in FIG. 1A, this exemplary color flow imaging system of the prior art obtains a number N of Complex Samples (CSs) 10 that are determined at a first given Location 12a in a region of interest for color flow mapping wherein N is at least 2. For purposes of the present discussion, the N CSs 10 are represented in FIG. 1A by two Complex Samples (CSs) 10a and 10b. As illustrated, CS 10a is shown as comprised of a Magnitude Component ($A_1$) 14a and a Phase Component ($\theta_1$) 16a and CS 10b is shown as comprised of a Magnitude Component ($A_2$) 14b and a Phase Component ($\theta_2$) 16b. CSs 10a and 10b may therefore be represented by Equations 18a and 18b, respectively, in FIG. 1B and the Autocorrelation Vector ($V_A$) 20a resulting from each pair of CSs 10, represented by CSs 10a and 10b, may be represented by Equation 18c-1, 18c-2 and 18c-3 in FIG. 1B wherein Equations 18c-2 and 18c-3 are the expanded and reduced forms of Equation 18c-1.

The autocorrelation processing of each pair of CSs 10, as represented by CSs 10a and 10b, will result in a VA 20a having an Autocorrelation Vector Real Component (Real VA) 20r expressed in Equation 18d-1 of FIG. 1B and an Autocorrelation Vector Imaginary Component (Imag $V_A$) 20i as expressed in Equation 18d-2 of FIG. 1B. It may be seen therein that the magnitude components $A_1$ 14a and $A_2$ 14b of CSs 10a and 10b affect the real and imaginary components Real $V_a$ 20r and Imag $V_a$ 20i of $V_a$ 20a and will therefore affect the color flow image resulting from the subsequent scan conversion of the $V_A$s 20a generated to create the color flow image.

Referring again to FIG. 1A and continuing the process as will be done to create a color flow image, the exemplary system of the prior art would then repeat the above described velocity vector autocorrelation process for a second given Location 12b that is different from but adjacent to Location 12a and again will obtain N CSs 10, represented in FIG. 1A for purposes of discussion by CS 10c and CS 10d. Again, and as illustrated, CS 10c is shown as comprised of a Magnitude Component ($B_1$) 14c and a Phase Component ($\gamma_1$) 16c and CS 10d is shown as comprised of a Magnitude Component ($B_2$) 14d and a Phase Component ($\gamma_2$) 16d. CSs 10c and 10d may therefore be represented by Equations 22a and 22b, respectively, in FIG. 1C and the Autocorrelation Vector ($V_B$) 20b resulting from CSs 10c and 10d may be represented by Equation 22c-1, 22c-2 and 22c-3 in FIG. 1 B wherein Equations 22c-2 and 22c-3 are the expanded and reduced forms of Equation 22c-1.

The autocorrelation processing of each pair of CSs 10, as represented by CSs 10c and 10d, will thereby again result in a VB 20b having an Autocorrelation Vector Real Component (Real VB) 20r as expressed in Equation 22d-1 of FIG. 1C and an Autocorrelation Vector Imaginary Component (Imag VB) 20i as expressed in Equation 22d-2 of FIG. 1C. It may be seen therein that the magnitude, or amplitude, components B. 14c and $B_2$ 14d of CSs 10c and 10d again affect the real and imaginary components Real $V_B$ 20r and Imag $V_B$ 20i of $V_B$ 20b and will therefore affect the color flow image resulting from the subsequent scan conversion of the autocorrelation vector from which the color flow image is created.

Referring now to FIG. 1C, the exemplary system of the prior art discussed herein will, after determining the autocorrelation vectors for an array of Locations 12 throughout the region of interest, perform two point or multiple point interpolation of the autocorrelation vectors to generate the final scan converted color flow image. Each interpolation will be between, respectively, the real and imaginary components of the autocorrelation vectors and the results of a single such interpolation between radially adjacent samples are illustrated by Equations 24-1 and 24-2 in FIG. 1C wherein Equation 24-1 represents the interpolation of the real components, (Real Int) 24r, of the autocorrelation vectors $V_A$ 20a and $V_B$ 20b and Equation 24-2 represents the interpolation of the imaginary components, (Imag Int) 24i, of the autocorrelation vectors $V_A$ 20a and $V_B$ 20b. It may be seen therein that the individual magnitude components of the velocity vectors not only again affect the real and imaginary components after the radial interpolation. The results of all radial interpolations would then be further interpolated between adjacent angular lines in a manner described in U.S. Pat. No. 4,471,449, issued Sep. 1, 1984 to Leavitt et al., resulting in final scan converted autocorrelation vectors. Therefore, the full dynamic range must be preserved through scan conversion in order to insure proper velocity calculations from the real and imaginary components of the autocorrelation vectors using a trigonometric relationship to derive phase.

B. Method of the Present Invention for Color Flow Mapping (FIGS. 2A, 2B and 2C)

Referring now to FIGS. 2A, 2B and 2C, therein is illustrated the method of the present invention for generating the autocorrelation vectors from which the velocity images are generated, thereby simplifying the scan conversion of the real and imaginary components of the autocorrelation vector since the components are normalized to a unit vector. The amplitude data is represented in a separate scan conversion, which thereby does not need to carry the full resolution of the dynamic range since the amplitude data is used for segmentation only.

To reiterate briefly it has been described above that the complex samples obtained from the returned ultrasonic scan line signals includes both magnitude and phase components such that the resulting autocorrelation vectors obtained for pairs of complex samples contain components affected by the magnitude, or amplitude, or the scan line signals. This is illustrated in FIG. 2A in Equations 26a-1 and 26a-2, which appeared previously as Equations 18c-3 and 22c-3 in the above discussion of a typical system of the prior art. As will be understood by those of ordinary skill in the relevant arts, and as may be seen from Equations 18d-1, 18d-2, 22d-1 and 22d-2 above, Equations 26a-1 and 26a-2 contain both the real and imaginary components of the autocorrelation vectors, as respectively the cosine and sine components of the expressions, and it may be seen that the amplitude components of the velocity vectors appear in both the real and imaginary components of the autocorrelation vectors.

1. Basic Principle of Operation of the Present Invention (FIG. 2B)

According to the present invention, this effect is eliminated in a color flow processing system implemented according to the present invention by operating upon the real and imaginary components of each autocorrelation vector to "strip off", that is, to separate, the amplitude information from each autocorrelation vector, thereby resulting in autocorrelation vectors having unity amplitude, and processing the amplitude information separately.

As a consequence, and as illustrated in FIG. 2B, the transformed autocorrelation vectors $V_A$ 20a' and $V_B$ 20b' generated according to the present invention and corresponding respectively to $V_A$ 20a and $V_B$ 20b as expressed in Equations 26a-1 and 26a-2 are expressed in Equations 28a-1 and 28a-2 respectively, while the real and imaginary components of $V_A$ 20a' and $V_B$ 20b', respectively Real $V_A$ 20r', Imag $V_A$ 20I', Real $V_B$ 20r' and Imag $V_B$ 20I', are expressed in Equations 28b-1, 28b-2, 28c-1 and 28c-2 respectively. As may be seen from Equations 28a-1, 28a-2, 28b-1, 28b-2, 28c-1 and 28c-2, the autocorrelation vectors of the present invention are unity amplitude vectors having the same angle, or phase, components as $V_A$ 20a and $V_B$ 20b, but with unity amplitude. $V_A$20' and $V_B$20' thereby contain only components that are dependent upon and reflect only the phase, or angle, components of the velocity vectors.

As a result, the real and imaginary interpolation components, Real Int 24r' and Imag Int 24i', of each pair of interpolated unity amplitude transformed autocorrelation vectors, such as $V_A$ 20a' and $V_B$ 20b', are as expressed in Equations 28-1 and 28-2, respectively. As will be obvious, these interpolation results are achieved without the necessity of carrying the dynamic range of the original autocorrelation components since the vector has unity amplitude. The interpolated results convey the phase information, which in turn determines the velocity. The magnitude of the autocorrelation and the two dimensional components are used for segmentation.

2. Exemplary System Implementing the Present Invention (FIG. 3A)

It will be apparent from the above description of the basic principles of operation of a color flow imaging system according to the present invention that the separation of the velocity vector amplitude information from the autocorrelation vectors and separate processing of the unity amplitude autocorrelation vectors and the velocity vector amplitude information essentially allows the system to generate three different types of information for use in generating color flow images. The first type of information is the unity amplitude autocorrelation vectors which has two components, the real (cosine) and imaginary (sine) components of the autocorrelation vectors and represent flow velocity information independent of the autocorrelation vector amplitude. The other two types of information are amplitude related information, one being the compressed amplitude component of the autocorrelation vectors that is separated from the real and imaginary components of the unity amplitude autocorrelation vectors and the other being the two dimensional (2D) image amplitude information.

To illustrate by means of an exemplary system incorporating the present invention, and referring to FIG. 3A, therein is shown a block diagram of a color flow imaging System 30 implementing the present invention. As represented therein, System 30 includes a Scan Array 32 comprised of an array of ultrasonic transducer transmit/receive elements for transmitting scan lines into the region of interest for imaging and for receiving the return scan lines containing imaging and flow velocity information. Scan Array 32 is connected, in turn, to and from Beam Former 34 which contains the switching and phase control circuitry to form the transmitting and receiving lines of Scan Array 32. The received signals are passed to Detection and Processing 36, which performs, for example, the detection, frequency shifting and filtering operations necessary to generate Complex Samples (CSs) 10, as described above.

In a typical system implementing the present invention, Autocorrelator 38 would follow the Detection and Processing 36 function producing the signals Real 20$r$ and Imag 20$i$. As described, the function of Autocorrelator 38 is the generation of autocorrelation vectors between pairs of CS 10 of at least one input set of N CSs 10 wherein N is at least two and wherein each autocorrelation vector includes both amplitude and phase information. Additional processing would follow with Post Autocorrelator Processing 40 function producing Real 20$r'$ and Imag 20$i'$. This processing may include resampling, noise bias compensation, gain normalization, flash reduction, spatial filtering and frame to frame persistence. Each processing step is known to those of ordinary skill in the arts. Resampling involves the calculation of intermediate samples at a prescribed sampling period. Noise compensation is an additive calculation to all autocorrelation vectors based on a bias present when the system is operated without any transmit stimulus, that is, with random noise only. Gain normalization is readjusting the number of bits needed to characterize the signal and is a form of normalization based on system settings. Flash reduction is removing all autocorrelation vectors that exceed limits defining the maximum expected signal levels. Spatial filtering is a smoothing operation performed on the autocorrelation results used to reject high frequency content. Frame to frame persistence is a lossy Infinite Impulse Response filter used to blend frames.

The outputs of Post Autocorrelator Processing 40 are inputs to both the Amplitude Detection 46 and Unit Vector Conversion 42 function blocks. The function of Amplitude Detection 46 is to perform magnitude assessment of the autocorrelation vector. One straightforward way is to calculate the square root of the sum of the squares of Real 20$r'$ and Imag 20$i'$. However, one skilled in the arts could equally as well use a LUT or some other means to perform this function. The output of Amplitude Detection 46 is provided as an input to the Compression 48 function. This function compresses the amplitude range into a smaller set of bits at its output, CompAD 50.

Unit Vector Conversion 42 operates to generate a corresponding unity amplitude autocorrelation vector for each processed input set of N CSs 10 wherein the phase of each unit amplitude autocorrelation vector is the same as the resultant autocorrelation vector. The function of Unit Vector Conversion 42 is thereby to convert the Real 20$r'$ and Imag 20$i'$ to unit amplitude components Real 20$r''$ and Image 20$i''$ representing the cosine and sine of the autocorrelation vector angle and thus preserving the angle of the vector. The magnitude of the vector is preserved in CompAD 50.

The three outputs, Real 20$r''$, Imag 20$i''$ and CompAD 50, are inputs to Scan Convertor 44. An additional input, Two Dimensional (2D) Data 54 is supplied as an additional output from Detection and Processing 36. 2D Data 54 is generated in Detection and Processing 36 by using log detection and filtering functions as necessary to extract the 2D image amplitude information from the received scan line signal.

As indicated, Scan Converter 44 generates images from the four types of image data and, in the present embodiment, operates on each in separate passes to form four corresponding types of image. The two scan converted image of the Real 20$r''$ and Imag 20$i''$ pass as inputs to Velocity Calculation 52 wherein the velocity is determined on a pixel by pixel basis corresponding to the arctangent (Imag 20$i''$/Real 20$r''$). The velocity calculation may be done using a LUT or in software. The output from Velocity Calculation 52 is an input to Segmentator 56, as are the scan converted CompAD 54 and the scan converted 2D Data 54. The decision of which image data will be displayed, such as 2D image data or velocity data from the autocorrelation vectors, is made on a pixel by pixel basis by Segmentator 56, which operates using stored decision criteria and as a function of the velocity values, the magnitude of flow values and the 2D image values and the type of imaging being performed. The decision of which image data to display, again on a pixel by pixel basis, may also be performed, or overridden, by a User Display Select input 58.

3. Presently Preferred Embodiment of the Present Invention (FIG. 3B)

Figure 3B:
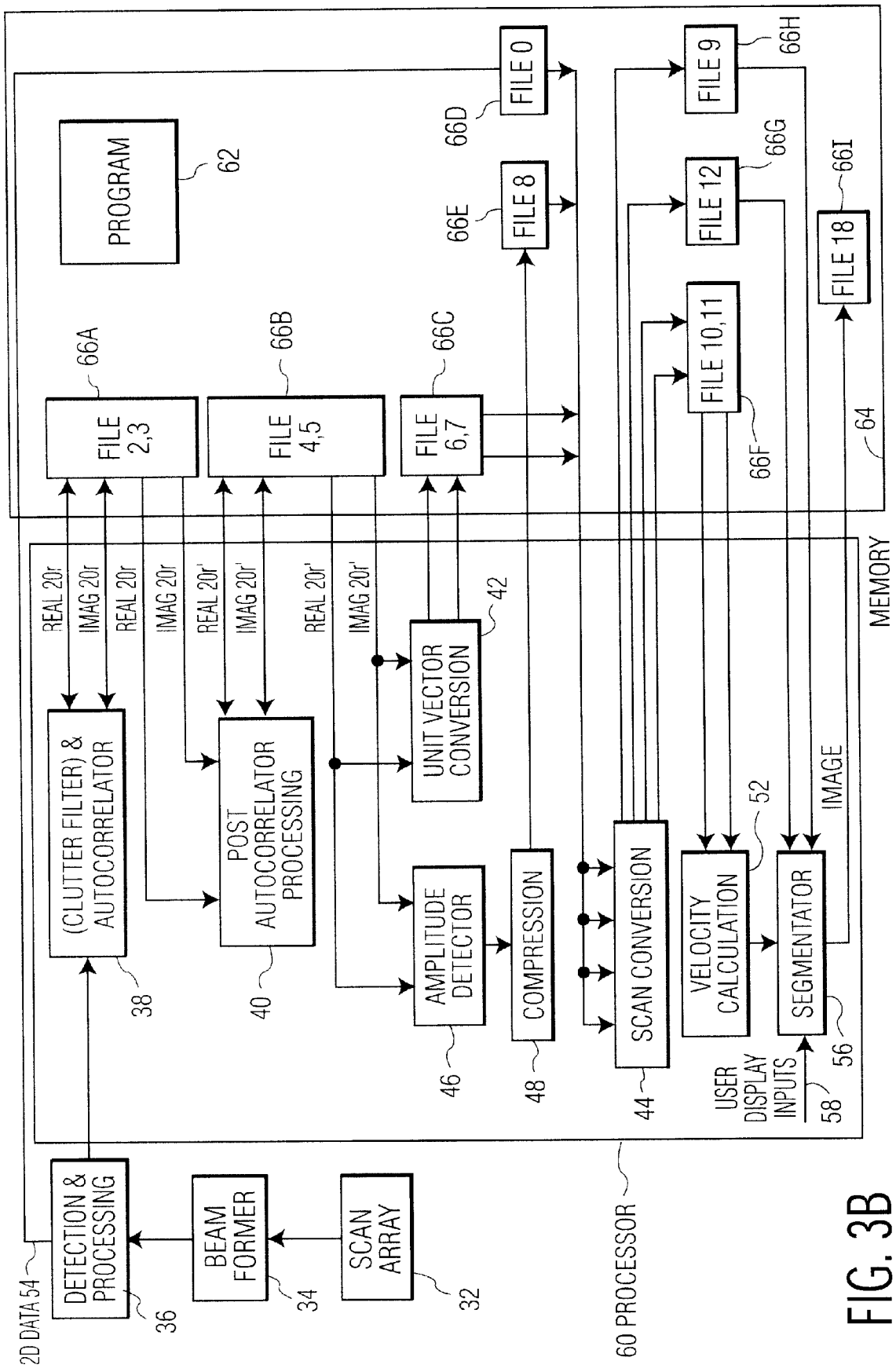
FIG. 3B is a block diagram of a presently preferred embodiment of the present invention.

Referring now to FIG. 3B, therein is shown a block diagram representation of a presently preferred embodiment of the present invention as described above with reference to FIG. 3A, and this embodiment is further described in the program listing in the attached Appendix. It should be noted that the single or double digit numeric designations appearing in the lower right hand corner of each of Files 66 in FIG. 3B each corresponds to a "buffer_filexx" reference appearing in the program listings of the Appendix, wherein each numeric designation corresponds to the "xx" component of the corresponding buffer_filexx references.

As illustrated in FIG. 3B, Scan Array 32, Beam Former 34, Detection and Processing 36, Autocorrelator 38, Scan Convertor 44, Velocity Calculation 52 and Segmentator 56 are as found in a conventional color flow ultrasonic imaging system, as are available from a number of manufacturers, such as Hewlett-Packard, and the structure, operation and construction of these components will be well understood by those of ordinary skill in the relevant arts. As is also well known and understood, certain of Beam Former 34, Detection and Processing 36, Autocorrelator 38, Scan Convertor 44, Velocity Calculation 52 and Segmentator 56 may be implemented as functions executed by a processor operating under program control while others may be implemented in hardware logic and circuitry, with the choice of implementation typically being made on the basis of the required processing speed, which in turn is determined by the function being performed and the volume of data to be operated upon.

As will also be apparent from the following description of a presently preferred embodiment of the invention, the component parts and functions of the present invention may be added to an existing system, or a new system specifically designed to incorporate the present invention may be constructed. In either instance, the present invention is preferably implemented as functions and operations executed by a processor operating under program control as ultrasonic imaging systems typically include a processor operating under program control, thereby simplifying the addition of the present invention to existing systems. It will be appreciated, however, that at least certain functions and operations of the present invention may also be implemented in hardware logic and circuitry, depending upon the requirements of the system in which the invention is implemented.

FIG. 3B illustrates an embodiment of the present invention as preferably implemented by a processor operating under program control, and the following discussion will focus on the operation of the present invention as implemented as a program controlled process, all other aspects of the operation of a system employing the present invention having been described above. In this regard, it will be seen that FIG. 3B reflects FIG. 3A with modifications to illustrate the functions of the present invention as performed by a Processor 60 operating under control of a Program 62 residing in a Memory 64 and storing data generated by the processes of the present invention in Data File(s) 66 residing in a Memory 64. It will also be appreciated by those or ordinary skill in the relevant arts that the file structures represented in FIG. 3B are exemplary and illustrative and that a variety of file structures may be implemented to perform the same functions, depending upon the choices of the designer, the types of data stored therein, the relationships between the various types of data, and the amount of data processed or generated by each function.

As illustrated in FIG. 3B, Real 20r and Imag 20r generated by Autocorrelator 38 are written into a File(s) 66A in Memory 64 and are read therefrom for use in the Post Autocorrelation Processing 40 process by Processor 60 operating under control of Program 62. The results of the Post Autocorrelation Processing 40 process, Real 20r' and Imag 20r', are written by Processor 60 into File(s) 66B, and are read therefrom for use in the Unit Vector Conversion 42 and Amplitude Detector 46 processes. The output of Unit Vector Conversion 42 is written into File 66C, while the output of Amplitude Detector 46 is passed to Compression 48 and the output of Compression 46 written into File 66E. At the same time, and as shown in FIG. 3B, the 2D Data 54 from Detection and Processing 36 is written into File 66D. The information residing in Files 66C, 66E and 66F is then passed to Scan Converter 44, and the outputs of Scan Converter 44 are written into Files 66F, 66G and 66H. The information stored in File 66F is read and processed by Velocity Calculation 52 and the output of Velocity Calculation 52 being passed to Segmentator 56 while the information from Files 66G and 66H are passed directly to Segmentator 56. As shown, Segmentator 56 also receives User Display Inputs 58, and the Image output of Segmentator 56 is stored in a File 66I for subsequent use.

As described above, listings of a Program 62 implementing the present invention is provided in the attached Appendix and is related to FIG. 3B by means of the correspondence between the "buffer_filexx" references appearing in the program listing and the numeric designators appearing in the lower right hand corners of Files 66 in FIG. 3B, so that the program listing in the Appendix may be referred to for further details of a program controlled implementation of the present invention. It will be understood by those of ordinary skill in the relevant arts that other programs for implementing the present invention may be readily generated given the above descriptions of the present invention, and that many variations or modifications of such programs will be apparent to those of ordinary skill in the arts. It will also be noted, upon examination of the Appendix, that while Scan Convertor 44 is presently preferably implemented in hardware logic and circuitry because of the processing speed requirements of the scan conversion process, the Appendix also includes a program controlled implementation of the scan conversion process as an alternate embodiment.

It will be seen from the above descriptions of the present invention that the system of the present invention is advantageous in allowing segmentation based upon three forms of image data on a pixel by pixel basis. For example, the difference between 2D magnitude image data and flow magnitude image data arise from the processing of the received data. That is, the 2D image data processing path generally involves the log detection and filtering of the received signal data while the flow image data path generally includes the clutter filtering, autocorrelation, flash reduction, spatial filtering and noise bias compensation of the received signal data. It is therefore apparent that the spectral content of the two forms of data will be significantly different. These differences in the forms of the image data may in turn be utilized to optimize the displayed images depending upon the type of region and image to be displayed. For example, in cardiac applications where relatively large volumes are involved, such as the chambers of the heart, and there is minimal clutter, segmentation based on flow magnitude and flow velocity would be used to display the scanned image data. In the imaging of abdominal regions, such as the kidney or liver, segmentation based on flow velocity and 2D amplitude data would be used. In the instance of large blood vessels, a combination of flow velocity, flow amplitude and 2D amplitude data would be used.

It will also be appreciated by those of skill in the relevant arts that the method and system of the present invention offers other advantages over the systems of the prior art. For example, as described above the real and imaginary components of the transformed unity amplitude autocorrelation vectors used to generate flow velocity images contain only components dependent upon the phase or angle components of the velocity vectors and contain no signal amplitude dependent components, thereby avoiding the need to carry a wide dynamic range of signal data through the scan convertor. While the image data representing the compressed amplitude of the autocorrelation vectors, contains amplitude information, this information is not used in determining flow velocities. Although this amplitude information may be used in certain applications as a component of the segmentation process, the data processing paths are separate and the resulting image data is fundamentally different from that provided from the systems of the prior art.

In yet another advantage of the method and system of the present invention, and as described just above, the method and system of the present invention offers enhanced segmented display of data by providing three separate and independent forms of data, each of which may be used in any combination and on the basis of pixel by pixel decisions, to generate the optimum image display after segmentation.

Also, the method and system of the present invention allow a simpler and less complex implementation as the processing paths of the system are not required to process and accommodate the entire, uncompressed dynamic range of the real and imaginary components of the autocorrelation vectors entirely through the processing paths to the scan conversion stage as the dynamic amplitude range of the received data is carried in a separate, compressed processing path. In contrast, and even if the amplitude components of the autocorrelation vectors were compressed, rather than the autocorrelation vectors being transformed into unity amplitude correlation vectors, the correlation vectors would still have to be decompressed prior to the determination of velocity, thereby again requiring an increased dynamic range of the processing paths.

Lastly, it will be noted that while the presently preferred implementation of the method and system of the present invention uses a single scan converter for all four forms of data, the system could be implemented with multiple scan converters to provide an increase in processing speed or with each scan converters tailored to a particular form of data.

While the invention has been particularly shown and described with reference to preferred embodiments of the apparatus and methods thereof, it will be also understood by those of ordinary skill in the art that various changes, variations and modifications in form, details and implementation may be made therein without departing from the spirit and scope of the invention as defined by the appended claims. For example, it will be apparent that the present invention may be implemented as dedicated hardware circuits, as processes executed on a general purpose computer controlled by computer programs, or by a combination thereof. In further example, it will be understood by those of ordinary skill in the relevant arts that the number N of complex samples obtained for autocorrelation at each sampling point will depend upon a number of factors, such as the desired resolution of the system, but will be 2 or greater. It will also be understood that many systems, depending upon the initial signal processing sampling rate, will not require resampling. Therefore, it is the object of the appended claims to cover all such variation and modifications of the invention as come within the true spirit and scope of the invention.

What is claimed is:

1. In an ultrasonic color flow imaging system including an ultrasonic scan array of transducer elements for transmitting and receiving ultrasonic scan lines, a beamformer for forming transmitting and receiving scan lines, and a scan line signal processor for detecting received scan lines and generating complex samples representing image flow information wherein each complex sample includes an amplitude component and a phase component, a flow velocity processor having reduced dynamic range requirements for subsequent scan conversion of velocity image information, comprising:

an autocorrelation vector processor for
generating a resultant autocorrelation vector between pairs of complex samples of at least one input set of N complex samples wherein N is at least two and wherein each resultant autocorrelation vector includes an amplitude component and a phase component, and a unit vector converter for
generating for each resultant autocorrelation vector a corresponding unity amplitude autocorrelation vector for each processed input set of N complex samples, the phase of each unit amplitude autocorrelation vector being the same as the resultant autocorrelation vector, and
providing the unity amplitude autocorrelation vectors to a scan converter for subsequent scan conversion and generation of a color flow image.

2. The flow velocity processor of claim 1 for generating color flow image data, further comprising:

a two dimensional image data processing path for
extracting two dimensional image data from the received scan lines, and
providing the two dimensional image data to the scan converter for the generation of a segmented image.

3. The flow velocity processor of claim 1 for generating color flow image data, further comprising:

an autocorrelation vector amplitude information processing path for
extracting the amplitude component of each resultant autocorrelation vector,
generating compressed resultant autocorrelation vector amplitude information, and
providing the compressed resultant autocorrelation vector amplitude information to the scan converter for the generation of a segmented image.

4. An improved ultrasonic segmentation imaging system providing reduced dynamic range requirements for scan conversion of velocity image information, the system including an ultrasonic scan array of transducer elements for transmitting and receiving ultrasonic scan lines, a beamformer for forming transmitting and receiving scan lines and comprising:

a scan line signal processor for detecting received scan lines and generating complex samples representing image flow information wherein each complex sample includes an amplitude component and a phase component, a color flow image processor, including
an autocorrelation vector processor for
generating a resultant autocorrelation vector between pairs of complex samples of at least one input set of complex samples wherein N is at least two and wherein each resultant autocorrelation vector includes an amplitude component and a phase component, and
a unit vector converter for
generating for each resultant autocorrelation vector a corresponding unity amplitude autocorrelation vector for each processed input set of N complex samples, the phase of each unit amplitude autocorrelation vector being the same as the resultant autocorrelation vector, and a two dimensional image data processor for
extracting two dimensional image data from the received scan lines, and
a scan converter for receiving the unity amplitude autocorrelation vectors and the two dimensional image data and providing scan converted image data to a segmentator for generation of a segmented image.

5. The improved ultrasonic segmentation imaging system of claim 4, further comprising:

an autocorrelation vector amplitude information processor for
extracting the amplitude component of each resultant autocorrelation vector,
generating compressed resultant autocorrelation vector amplitude information, and
providing the compressed resultant autocorrelation vector amplitude information to the scan converter for the generation of a segmented image.

6. In an ultrasonic color flow imaging system including an ultrasonic scan array of transducer elements for transmitting and receiving ultrasonic scan lines, a beamformer for forming transmitting and receiving scan lines, and a scan line signal processor for detecting received scan lines and generating complex samples and representing image flow information wherein each complex sample includes an amplitude component and a phase component, a method for flow velocity processing having reduced dynamic range requirements for subsequent scan conversion of velocity image information, comprising the steps of:

generating a resultant autocorrelation vector between pairs of complex samples of at least one input set of N complex samples wherein N is at least two and wherein each resultant autocorrelation vector includes an amplitude component and a phase component, and generating for each resultant autocorrelation vector a corresponding unity amplitude autocorrelation vector for each processed input set of N complex samples, the phase of each unit amplitude autocorrelation vector being the same as the resultant autocorrelation vector, and providing the unity amplitude autocorrelation vectors to a scan converter for subsequent scan conversion and generation of a color flow image.

7. The method of claim 6 for generating color flow image data, further comprising the steps of:

extracting two dimensional image data from the received scan lines, and providing the two dimensional image data to the scan converter for the generation of a segmented image.

8. The method of claim 6 for generating color flow image data, further comprising the steps of extracting the amplitude component of each resultant autocorrelation vector, generating compressed resultant autocorrelation vector amplitude information, and providing the compressed resultant autocorrelation vector amplitude information to the scan converter for the generation of a segmented image.

9. For use in an ultrasonic imaging system, an improved method for the generation of ultrasonic segmented images providing reduced dynamic range requirements for scan conversion of velocity image information, the system including an ultrasonic scan array of transducer elements for transmitting and receiving ultrasonic scan lines, and a beamformer for forming transmitting and receiving scan lines and the method comprising the steps of:

detecting received scan lines and generating complex samples representing image flow information wherein each complex sample includes an amplitude component and a phase component, generating flow velocity image information by generating a resultant autocorrelation vector between pairs of complex samples of at least one input set of N complex samples wherein N is at least two and wherein each resultant autocorrelation vector includes an amplitude component and a phase component, and generating for each resultant autocorrelation vector a corresponding unity amplitude autocorrelation vector for each processed input set of N complex samples, the phase of each unit amplitude autocorrelation vector being the same as the resultant autocorrelation vector, generating two dimensional image information by extracting two dimensional image data from the received scan lines, and providing the unity amplitude autocorrelation vectors and the two dimensional image data to a scan converter and a segmentator for generation of a segmented image.

10. The method of claim 9, further comprising the steps of:

generating velocity amplitude image information by extracting the amplitude component of each resultant autocorrelation vector, generating compressed resultant autocorrelation vector amplitude information, and providing the compressed resultant autocorrelation vector amplitude information to the scan converter for the generation of a segmented image.

* * * * *